United States Patent
Grobe et al.

(10) Patent No.: US 12,343,464 B2
(45) Date of Patent: Jul. 1, 2025

(54) TECHNIQUES FOR DETERMINING DIALYSIS PATIENT PROFILES

(71) Applicant: Fresenius Medical Care Holdings, Inc., Waltham, MA (US)

(72) Inventors: Nadja Grobe, Huntington, NY (US); Peter Kotanko, New York, NY (US); Xia Tao, West New York, NJ (US); Stephan Thijssen, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1132 days.

(21) Appl. No.: 17/162,012

(22) Filed: Jan. 29, 2021

(65) Prior Publication Data
US 2021/0236705 A1 Aug. 5, 2021

Related U.S. Application Data

(60) Provisional application No. 62/967,743, filed on Jan. 30, 2020.

(51) Int. Cl.
*A61M 1/16* (2006.01)
*A61M 1/14* (2006.01)
(Continued)

(52) U.S. Cl.
CPC .......... *A61M 1/1619* (2014.02); *A61M 1/159* (2022.05); *A61M 1/1609* (2014.02);
(Continued)

(58) Field of Classification Search
CPC .......... A61M 1/14; A61M 1/15; A61M 1/152; A61M 1/155; A61M 1/159; A61M 1/16;
(Continued)

(56) References Cited

U.S. PATENT DOCUMENTS

2011/0009810 A1 1/2011 Lo et al.
2011/0010101 A1 1/2011 Lo
(Continued)

FOREIGN PATENT DOCUMENTS

| JP | 2012532669 A | 12/2012 |
| WO | 03063929 A1 | 8/2003 |
| WO | 2006002483 A1 | 1/2006 |

OTHER PUBLICATIONS

Sritippayawan et al, Proteomic analysis of peritoneal dialysate fluid in patients with different types of peritoneal membranes, Oct. 9, 2007, Journal of Proteome Research, vol. 6, pp. 4356-4362 (Year: 2007).*

(Continued)

*Primary Examiner* — Shefali D Patel
(74) *Attorney, Agent, or Firm* — KDW Firm PLLC

(57) ABSTRACT

Methods, apparatuses, and systems for determining a peritoneal transport status of a patient based on mass analyzing low volumes of peritoneal dialysis (PD) effluent to generate patient information that may be evaluated using PD effluent fingerprints to determine peritoneal transport characteristics of the patient are described. For example, in one embodiment, a method of determining a transport status of a dialysis patient may include obtaining a volume of peritoneal dialysis (PD) effluent of the dialysis patient, generating patient information via mass analysis of the volume of PD effluent, and determining patient profile information based on evaluating the patient information with a profile library, the patient profile information comprising a peritoneal transport status classification. Other embodiments are described.

16 Claims, 9 Drawing Sheets

(51) Int. Cl.
   *A61M 1/28*    (2006.01)
   *G01N 30/72*   (2006.01)
   *G16H 10/40*   (2018.01)

(52) U.S. Cl.
   CPC ............ *A61M 1/1613* (2014.02); *A61M 1/28* (2013.01); *A61M 1/152* (2022.05); *A61M 1/155* (2022.05); *A61M 2205/3313* (2013.01); *A61M 2205/3379* (2013.01); *A61M 2205/50* (2013.01); *A61M 2205/52* (2013.01); *A61M 2210/1017* (2013.01); *G01N 30/7233* (2013.01); *G16H 10/40* (2018.01)

(58) Field of Classification Search
   CPC ............ A61M 1/1601; A61M 1/1603; A61M 1/1605; A61M 1/1609; A61M 1/1613; A61M 1/1619; A61M 1/1654; A61M 1/28; A61M 1/287; A61M 2205/33; A61M 2205/3306; A61M 2205/3313; A61M 2205/3327; A61M 2205/3379; A61M 2205/50; A61M 2205/52; A61M 2210/1017; G01N 30/72; G01N 30/7233; G01N 30/728; G16H 10/40; H01J 49/00; H01J 49/04; H01J 49/0431; H01J 49/26
   See application file for complete search history.

(56) References Cited

U.S. PATENT DOCUMENTS

2017/0016908 A1   1/2017   Lundin et al.
2017/0045455 A1   2/2017   Robertson et al.

OTHER PUBLICATIONS

Csaicsich, D., et al., "Feasibility of Metabolomics Analysis of Dialysate Effluents from Patients Undergoing Peritoneal Equilibration Testing", Perit Dial Int. Sep.-Oct. 2015; 35(5): 590-592.
Asano, M., et al., "Differences in peritoneal solute transport rates in peritoneal dialysis", Clinical and Experimental Nephrology 23(1):122-134 (2018).
Tyan, Y-C., et al., "A comparative proteomics analysis of peritoneal dialysate before and after the occurrence of peritonitis episode by mass spectrometry", Clinica Chimica Acta 420:34-44 (2012).
International Search Report and Written Opinion for International application No. PCT/US2021/015696, mailed on May 18, 2021, 13 pages.
Eloot et al. J. of Inter. Soc. for Periton. Dialy. vol. 35(4) 2015. 436-42.
Bortolotti et al. (Paper) RSC Adv., 2016, 6, 112870-112876.
Wiesenhofer et al. Front Physiol., vol. 9, Article 1961, Jan. 21, 2019.
International Search Report and Written Opinion for International Application No. PCT/US2022/014233 mailed on May 11, 2022, 11 pages.
Wen Qiong et al. Biochem. and Biophys. Res. Comm, Elsevier, vol. 438, No. 3, 2013.
Salim Mujais et al., "Profiling of peritoneal ultrafiltration," Kidney International, vol. 62, Supplement 81, Oct. 2002, pp. S17-S22.

* cited by examiner

TECHNIQUES FOR DETERMINING DIALYSIS PATIENT PROFILES

CROSS-REFERENCE TO RELATED APPLICATION

This application claims the benefit of priority of 35 U.S.C. § 119(e) to U.S. Provisional Patent Application Ser. No. 62/967,743, filed on Jan. 30, 2020, which is incorporated by reference in its entirety as if fully set forth herein.

FIELD

The disclosure generally relates to determining physical characteristics of dialysis patients, and more particularly to processes for determining patient dialysis profile information indicative of the health of the patient and/or the success of peritoneal dialysis (PD) patients for the patient.

BACKGROUND

Patient treatment success in peritoneal dialysis (PD) is dependent on the functional and morphological integrity of the peritoneal membrane. In addition to functional failure of the peritoneum, long-term PD may lead to anatomical changes in the peritoneal tissues such as neoangiogenesis, vasculopathy and fibrosis, sometimes causing peritoneal sclerosis.

Accordingly, various patient characteristics are typically monitored during the course of PD treatment, including peritoneal transport status (i.e., transport across the peritoneal membrane for various solutes). However, conventional methods for determining peritoneal transport status (and/or other patient characteristics) are labor-intensive, time-consuming, and require extra patient clinic visits outside of regular PD treatment. Accordingly, PD patients and healthcare providers would benefit from processes capable of efficiently and effectively determining patient characteristics that may affect PD treatment without the drawbacks of conventional methods.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

The present disclosure relates generally to methods, apparatuses, and systems for determining a peritoneal transport status of a patient based on mass analyzing low volumes of peritoneal dialysis (PD) effluent to generate patient information that may be evaluated using PD effluent fingerprints to determine peritoneal transport characteristics of the patient. Other embodiments are described.

In one embodiment, a method of determining a transport status of a dialysis patient may include obtaining a volume of peritoneal dialysis (PD) effluent of the dialysis patient, generating patient information via mass analysis of the volume of PD effluent, and determining patient profile information based on evaluating the patient information with a profile library, the patient profile information comprising a peritoneal transport status classification.

In one embodiment, a method of performing dialysis for a dialysis patient may include performing a peritoneal dialysis (PD) process on the patient based on a peritoneal transport status, the peritoneal transport status determined via obtaining a volume of peritoneal dialysis (PD) effluent of the dialysis patient, generating patient information via mass analysis of the volume of PD effluent, and determining patient profile information based on evaluating the patient information with a profile library, the patient profile information comprising a peritoneal transport status classification.

In one embodiment, an apparatus may include at least one memory and logic coupled to the at least one memory, the logic to receive patient information generated via mass analysis of a volume of peritoneal dialysis (PD) effluent of a patient, and determine patient profile information based on evaluating the patient information with a profile library, the patient profile information comprising a peritoneal transport status classification In some embodiments, the mass analysis comprising one of liquid chromatography-mass spectrometry (LC-MS) or mass spectrometry (MS). In various embodiments, the volume obtained during routine dialysis of a patient. In various embodiments, the volume comprising less than or equal to about 1 milliliter (ml). In some embodiments, the peritoneal transport status classification comprising classifications of high, high-average, low-average, or low transporters based on solute transport characteristics. In various embodiments, a dialysis prescription may be determined based on the peritoneal transport status classification. In some embodiments, a dialysis treatment may be performed on the patient based on the peritoneal transport status classification.

BRIEF DESCRIPTION OF THE DRAWINGS

By way of example, specific embodiments of the disclosed machine will now be described, with reference to the accompanying drawings, in which.

DETAILED DESCRIPTION

Figure 1:
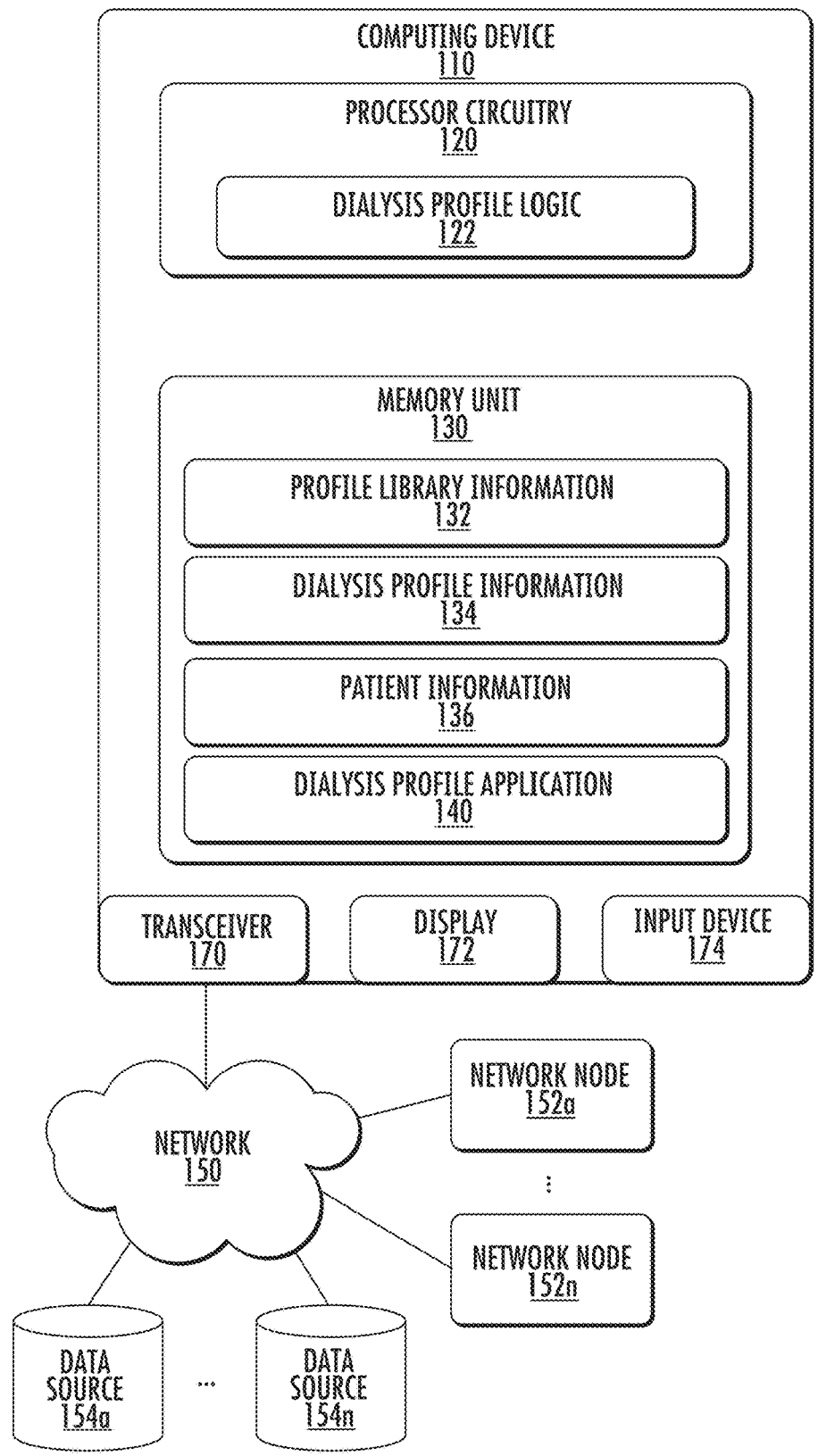
FIG. 1 illustrates a first exemplary operating environment according to some embodiments.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Patient treatment success in peritoneal dialysis (PD) is dependent on the functional and morphological integrity of the peritoneal membrane. In addition to functional failure of the peritoneum, long-term PD may lead to anatomical changes in the peritoneal tissues such as neoangiogenesis, vasculopathy and fibrosis, sometimes causing peritoneal sclerosis. Membrane characteristics alter especially after sustained use of non-physiological dialysis fluids. Accordingly, patient characteristics may be monitored over the duration of a PD patient treatment regimen to ensure, among other things, the health of patient peritoneal anatomy and/or the effectiveness of PD treatment. Non-limiting patient characteristics may include peritoneal transport status, dialysis adequacy, membrane characteristics, unexplained clinical changes, ultrafiltration failure, and/or the like. In some embodiments, a treatment recommendation, dialysis prescription, and/or dialysis treatment may be administered based on the patient characteristic determinations according to some embodiments.

The primary monitored characteristic may include peritoneal transport status for PD patients. In general, peritoneal transport status is a classification of membrane function by measuring the rate at which solutes equilibrate between the dialysate and body plasma. For example, the dialysate-to-plasma (D/P) ratio may operate to measure the combined effect of diffusion and ultrafiltration during DP. A low solute D/P means that transport across the peritoneal membrane for a given solute occurs slowly, and equilibrium between the dialysate and plasma is reached gradually. In contrast, a high solute D/P means that transport of a solute across the membrane occurs quickly, and equilibrium is reached sooner. D/P ratios are typically assessed for various solutes including urea, creatinine, and sodium.

Conventional tests for monitoring peritoneal transport status are generally time consuming, difficult for patients, and lack analysis of the full array of elements (for instance, metabolites) that may be used to form a complete assessment. For example, the standard peritoneal equilibration test (PET) is a 4-hour test developed over 30 years ago to assess peritoneal transport status in patients undergoing PD. The standard PET requires the collection of approximately 10 ml peritoneal effluent samples at certain time intervals and a mid-point blood sample. The solute transport rates are assessed by the rates of their equilibration between the peritoneal capillary blood and dialysate. As a proxy for all solutes, urea, creatinine, glucose, and sometimes sodium, are measured in the collected samples using different analytical tests. Patients are then categorized as high, high-average, low-average, or low transporters based on their solute transport characteristics.

As the PET is very labor-intensive and the time spent in the clinic by the patient to complete the standard PET is long and requires many lab samplings, a mini PET has been developed for follow-ups in response to clinical change. However, this modified version of the PET has shown inconsistencies compared to the standard PET. For both the standard PET and the mini PET, errors are possible due to sampling, data entry, calculations, and lab measurements. Another drawback is that the lab measurement for certain compounds may be affected by patient conditions that have to be corrected or otherwise managed. For example, creatinine may be incorrect due to high glucose concentrations and a correction factor is required for calculating the true creatinine amount.

Accordingly, some embodiments may provide a dialysis profile process operative to determine patient profile that may include a peritoneal transport status in a manner that is more efficient and effective than conventional methods, such as PET. Dialysis profile processes according to some embodiments may provide multiple technological advantages and improvements to technology, including computing technology, over conventional systems. In a non-limiting technological advantage, a dialysis profile process according to some embodiments may provide a more practical and personalized tool to evaluate dialysis adequacy, membrane characteristics, unexplained clinical changes, ultrafiltration failure, and/or the like. In a non-limiting technological advantage, a dialysis profile process according to some embodiments may use PD effluent that is collected from patients while at a clinic for routine checkups and/or the like; accordingly, no extra visits, such as are needed for PET, are required. In addition, the patient and healthcare team do not need to undergo a four-hour protocol. Instead, dialysis profile processes according to some embodiments may use PD effluent that may be routinely collected at scheduled monthly or quarterly visits. In some embodiments, a vast array of molecules (i.e., hundreds of molecules or greater), including, without limitation, urea, creatinine, and glucose, may be analyzed in less than 1 ml of PD effluent using a mass analysis, such as liquid chromatography (LC)-mass spectrometry (MS). In some embodiments, a dialysis profile process may categorize patients, for instance, as high, high-average, average, low-average, or low transporters based on their molecular fingerprints (see, for example, FIGS. 3 and 4). In various embodiments, untargeted and targeted LC-MS, MS, and/or the like approaches may be used to categorize patients (see, for example, FIGS. 5A and 5B). In various embodiments, a dialysis profile process may provide a personalized metabolomics-based transport test for peritoneal dialysis.

Accordingly, dialysis profile processes according to some embodiments may minimize the impact and intrusion of therapy on patients by reducing the number of extra visits to the clinic to determine transport status and providing accurate measurements of physical characteristics important for PD health and effectiveness. In addition, dialysis profile processes according to some embodiments may allow patient transport status to be monitored on a regular and routine basis, instead of only in the presence of warning signs as with conventional methods. As a result, reduced disease maintenance and interventions may lower the risk of infection, which is the second leading cause of death in dialysis patients, and other complications. Accordingly, dialysis profile processes according to some embodiments may operate to improve PD patient quality of life. Other technological advantages are described. Embodiments are not limited in this context.

In addition, dialysis profile processes according to some embodiments may be integrated into multiple practical applications. In one non-limiting practical application, dialysis profile processes may be integrated with providing a personalized metabolomics-based transport test for peritoneal dialysis. In one non-limiting practical application, dialysis profile processes may be integrated with providing a treatment recommendation, dialysis prescription, and/or dialysis treatment may be administered based on the patient characteristic determinations according to some embodiments. Other practical applications are described. Embodiments are not limited in this context.

The following Table 1 provides advantages of dialysis profile processes according to some embodiments versus PET tests:

TABLE 1

|  | Standard PET | Mini PET | Dialysis Profile Processes |
|---|---|---|---|
| Duration of test | 4 hours | 1 hour | <5 min |
| Sampling time points | Multiple | Twice | Once |
| Specimen | Blood, PD effluent | PD effluent | PD effluent |
| Volume of effluent | 10 ml | 10 ml | 1 ml (or less) |
| Visits | Extra dialysis access, increased risk of infection | | Routine, no additional connect/disconnect |
| Solutes | Urea, creatine, glucose, and sometimes sodium | Creatine, glucose | >1000 small molecules, including uremic toxins (urea, creatine) and glucose |
| Patient burden | High | Low | None |
| Staff burden | High | Low | None |
| Cost | Time commitment, 6 lab tests | Time commitment, 3 lab tests | Up to 12 lab tests per year |
| Frequency | As needed | As needed | Regularly |
| Drawbacks | Labor-intensive Errors due to sampling, data entry, calculations, and lab measurements Use of proxies to represent all solutes | Not equivalent to Standard PET | N/A |

FIG. 1 illustrates an example of an operating environment 100 that may be representative of some embodiments. As shown in FIG. 1, operating environment may include a computing device 110. In various embodiments, the functions, operations, configurations, data storage functions, applications, logic, and/or the like described with respect to computing device 110 may be performed by and/or stored in one or more other computing devices (not shown), for example, coupled to computing device 110 via a network 150 (i.e., network nodes 152a-n). A single computing device 110 is depicted for illustrative purposes only to simplify the figure. For example, operating environment 100 may include a plurality of computing devices 110 configured independently or in combination to perform aspects of embodiments described herein. Embodiments are not limited in this context.

Computing device 110 may include a transceiver 170, a display 172, an input device 174, and/or processor circuitry 120 that may be communicatively coupled to a memory unit 130. Processor circuitry 120 may be, may include, and/or may access various logics for performing processes according to some embodiments. For instance, processor circuitry 120 may include and/or may access a dialysis profile logic 122. Processing circuitry 120 and/or dialysis profile logic 122 and/or portions thereof, may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution, examples of which are provided by the exemplary computing architecture 700. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a proportional-integral-derivative (PID) controller, combinations of any of the foregoing, and/or the like.

Although dialysis profile logic 122 is depicted in FIG. 1 as being within processor circuitry 120, embodiments are not so limited. For example, dialysis profile logic 122 and/or any component thereof, may be located within an accelerator, a processor core, an interface, an individual processor die, implemented entirely as a software application (for instance, a dialysis profile application 140) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store profile library information 132, patient profile information 134, and/or patient information 136. In some embodiments, profile library information 132 may include information (or "fingerprints") used as a baseline to determine individual patient profiles (see, for example, FIGS. 2 and 3). In various embodiments, patient profiles may include peritoneal transport status, dialysis adequacy, membrane characteristics, unexplained clinical changes, ultrafiltration failure information and/or classification thereof. For example, a patient profile may include a classification of peritoneal transport status, such as the following categories: high, high-average, average, low-average, or low transporters. Embodiments are not limited to these categories, as patient profiles and/or peritoneal transport status may be categorized using various systems, such as a numeric category, grading (i.e., A-F), symbols, and/or the like. In some embodiments, patient profiles and information associated therewith (i.e., peritoneal transport status) may be stored as patient profile information 132.

In various embodiments, profile library information 132 may include mass analysis information of patients with known patient profiles. For example, profile library information 132 may include MS data of metabolites of patients with a known peritoneal transport status. In various embodiments, the profile library information 132 may include fingerprints, libraries, and/or the like generated from a population of patients so that, for example, patient information may be compared with the same or similar populations of patients (i.e., based on age, gender, disease progression, and/or the like) to determine a patient profile.

In some embodiments, patient information 136 may include information obtained about a patient via analysis of a patient sample, for example, such as blood or PD effluent. For example, in some embodiments, patient information may include MS data resulting from LC-MS and/or MS analysis of a volume of PD effluent. Although LC-MS and MS are used as examples, embodiments are not so limited. In some embodiments, for example, patient information 136 and/or profile library information 132 may be generated via various analytical instrument systems including, without limitation, a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system, or any combination thereof.

In some embodiments, the volume of PD effluent required to generate patient information 132 may be about 1 milliliter (ml) or less. In various embodiments, the volume of PD effluent may be about 0.001 ml, about 0.005 ml, about 0.01 ml, about 0.05 ml, about 0.1 ml, about 0.2 ml, about 0.3 ml, about 0.4 ml, about 0.5 ml, about 1.0 ml, about 1.5 ml, and/or any value or range between any two of these values (including endpoints).

In exemplary embodiments, profile library information 132, patient profile information 134, and/or patient information may be obtained from a remote data source, such as data store 154a-n and/or via network node 152a-n.

In some embodiments, dialysis profile logic 122, for example, alone or via dialysis profile application 140 may determine a patient profile for a patient based on patient information 136 and profile library information 132. For example, dialysis profile logic 122 may receive patient information 132 in the form of MS analysis results of a volume of PD effluent from the patient. Dialysis profile logic 122 may compare the MS analysis results to corresponding profile library information 132 (see, for example, FIGS. 2-4) to determine a matching profile. For example, the MS analysis results for Patient A may match with a high peritoneal transport status. Embodiments are not limited in this context.

Figure 2:
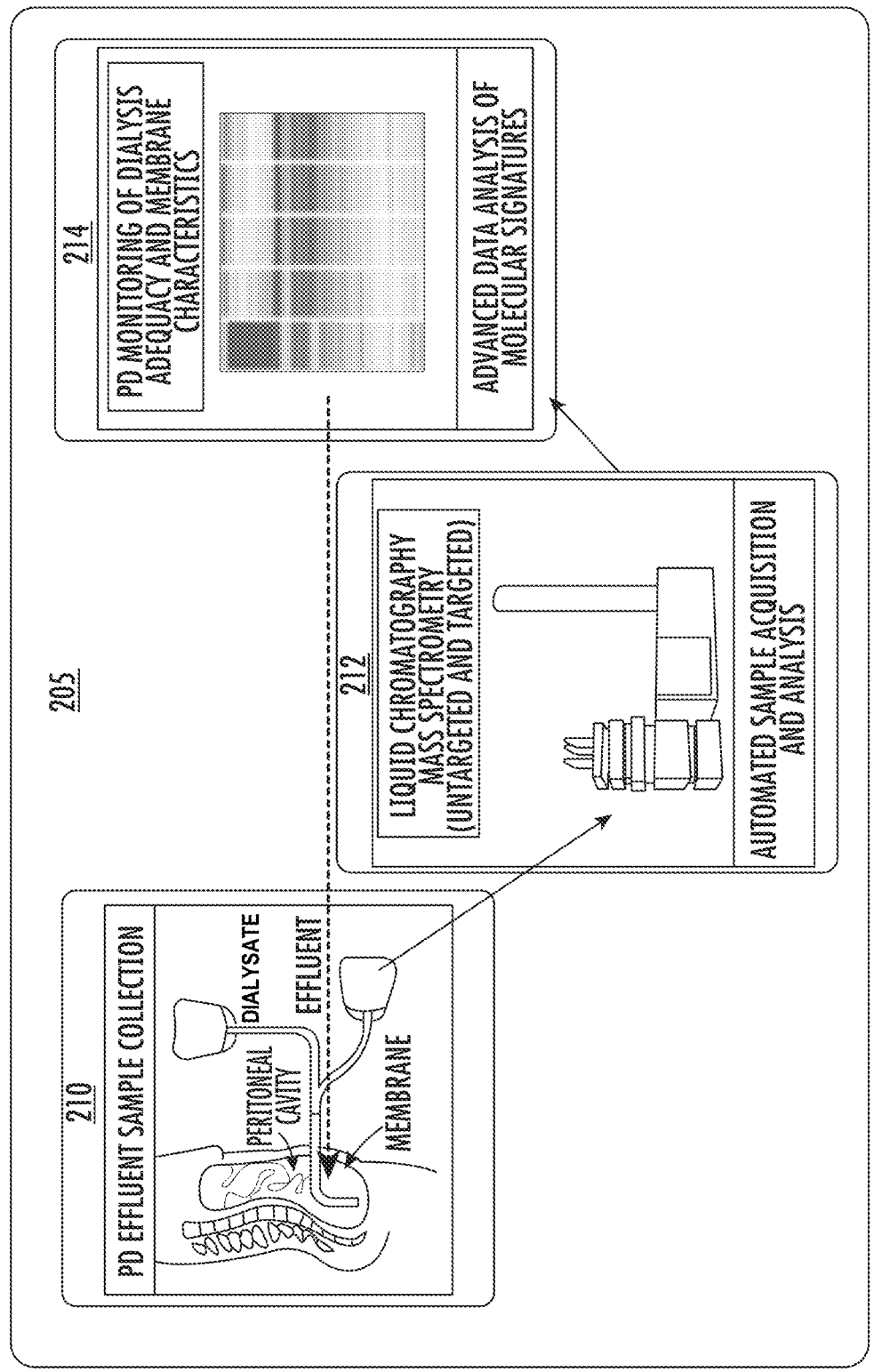
FIG. 2 illustrates a peritoneal dialysis (PD) profile process according to some embodiments.

FIG. 2 illustrates an example of an operating environment 200 that may be representative of some embodiments. As shown in FIG. 2, operating environment 200 depicts a process diagram for a dialysis profile process 205 according to some embodiments.

At block 210, dialysis profile process 205 may include obtaining a patient sample. In some embodiments, the patient sample may include PD effluent. For example, dialysis profile process may use less than 1 ml PD effluent that is collected from patients who come for routine checkups to a clinic (i.e., no extra visit has to be scheduled as compared with conventional methods). At block 212, a vast array of molecules, including urea, creatinine, and glucose, may be analyzed in less than 1 ml of PD effluent using analytical methods such as LC-MS and/or MS. At block 214, analysis of the results (i.e., from block 212) may be performed. For example, dialysis profile process 205 may include monitoring of patient characteristics via advanced data analysis of molecular signatures and/or the like.

Figure 3:
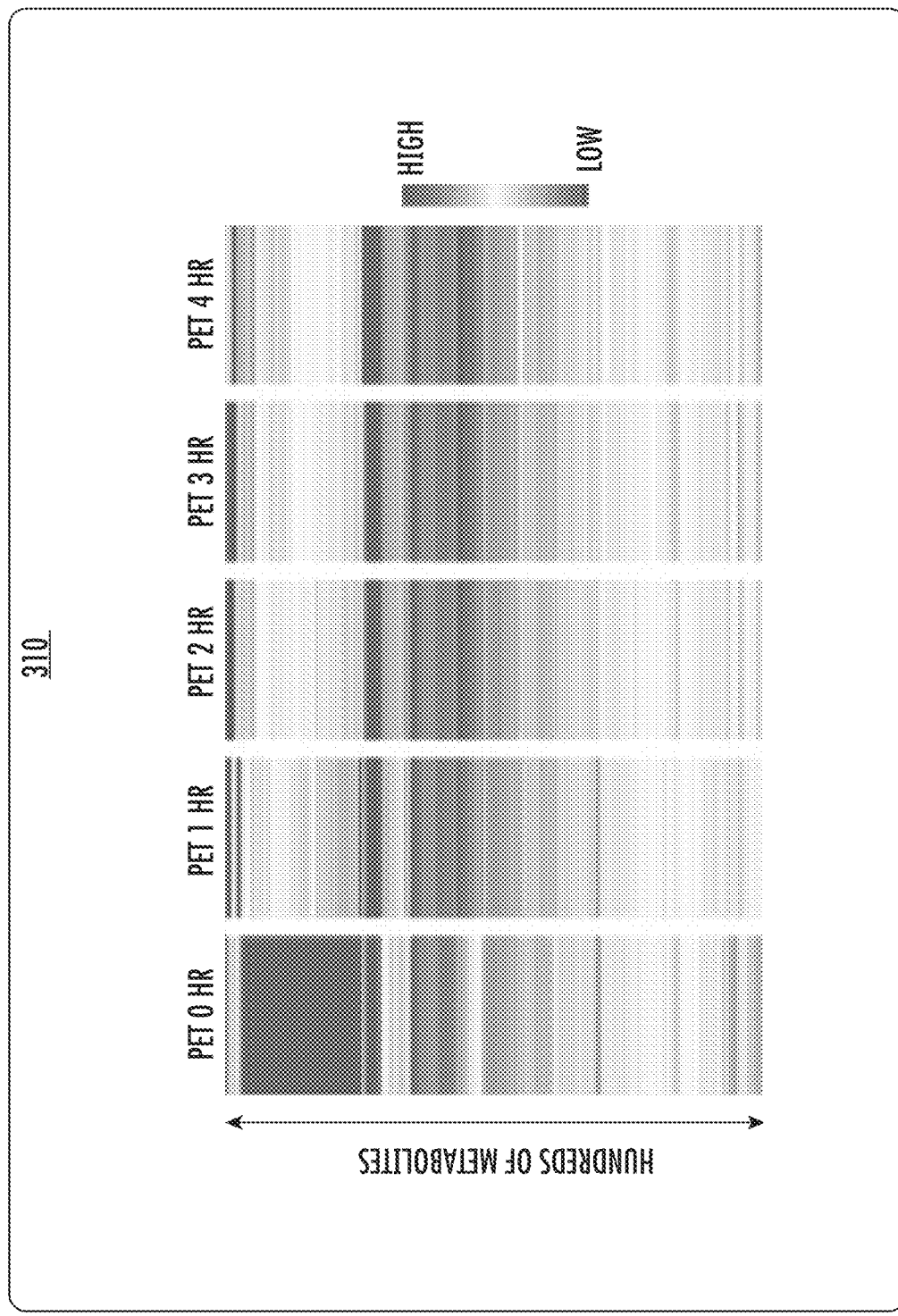
FIG. 3 illustrates PD profiles according to some embodiments.

FIG. 3 illustrates PD profiles according to some embodiments. As shown in FIG. 3, PDF profiles 305 (for example, a profile library or portion of a profile library) may be generated via analyzing a small amount of PD effluent (0.005 ml) at 0 hr, 1 hr, 2 hr, 3 hr, and 4 hr of a standard PET using LC-MS. Hundreds of molecules were detected with different abundances. These molecular fingerprints may be used to categorize patient profiles (e.g., peritoneal transport status, dialysis adequacy, membrane characteristics, and/or the like) of PD patients via a dialysis profile process according to some embodiments.

Figure 4:
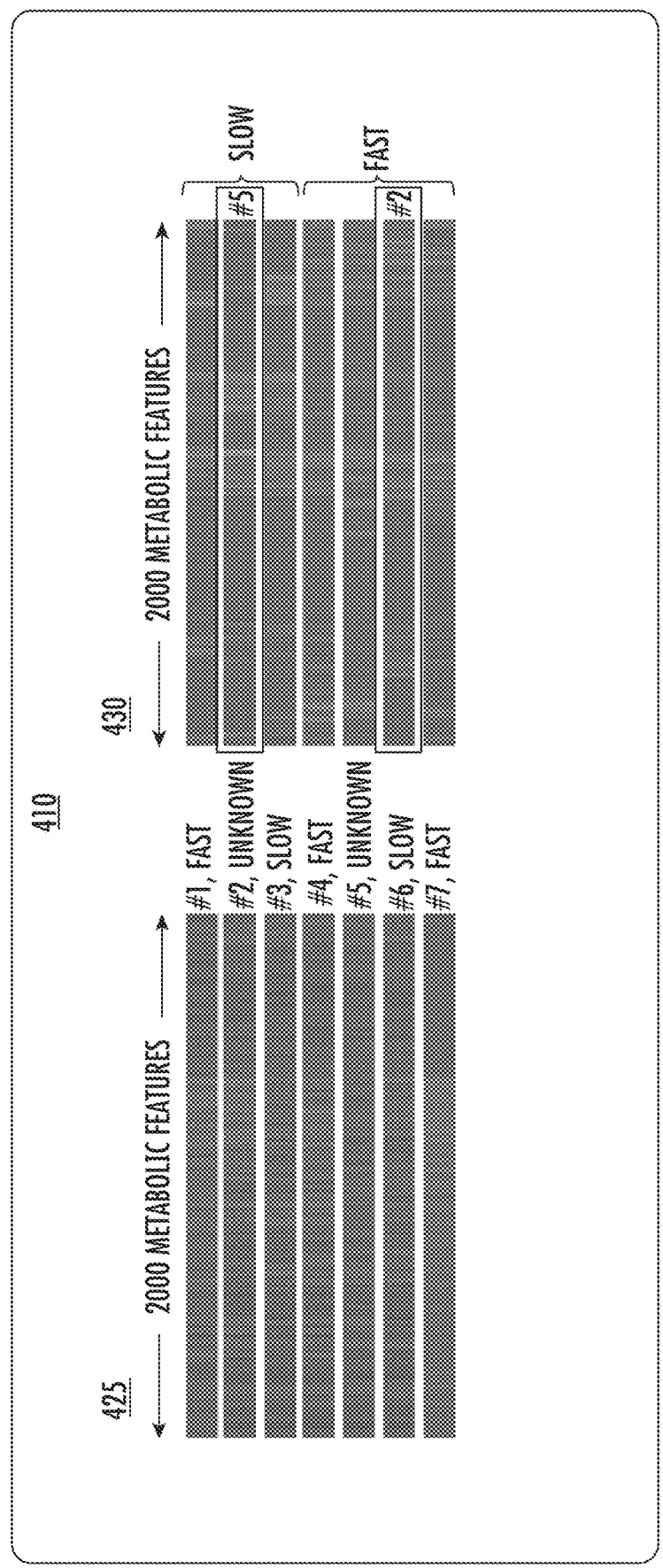
FIG. 4 illustrates PD profiles according to some embodiments.

FIG. 4 illustrates PD profiles according to some embodiments. As shown in FIG. 4, PD profiles 405 may include, for example, a profile library or portion of a profile library. In some embodiments, metabolomics may be used to characterizes PD effluent over time and associate individual temporal changes with transport status to trigger an adjustment of dialysis prescription or other intervention. For example, dialysis profiling processes according to some embodiments may provide a molecular fingerprinting platform operative to detect metabolites, including, for instance, unknown and/or previously uncategorized metabolites.

In the example of FIG. 4, seven routinely collected PD effluent samples were analyzed, of which five PD samples had the known transporter type "fast" or "slow" (425). For example, a small amount of PD effluent (0.005 ml) from a routine visit was analyzed using LC-MS. As shown in FIG. 4, hundreds of molecules were detected with different abundances. Two unknown samples were assigned to either "fast" or "slow" categories based on analysis with known metabolic fingerprints (430). A non-limiting example of an analysis of unknown samples with known metabolic fingerprints may include hierarchical clustering. For example, in 430, hierarchical cluster analysis may delineate differences of molecular fingerprints with peritoneal transport status.

Figure 5A:
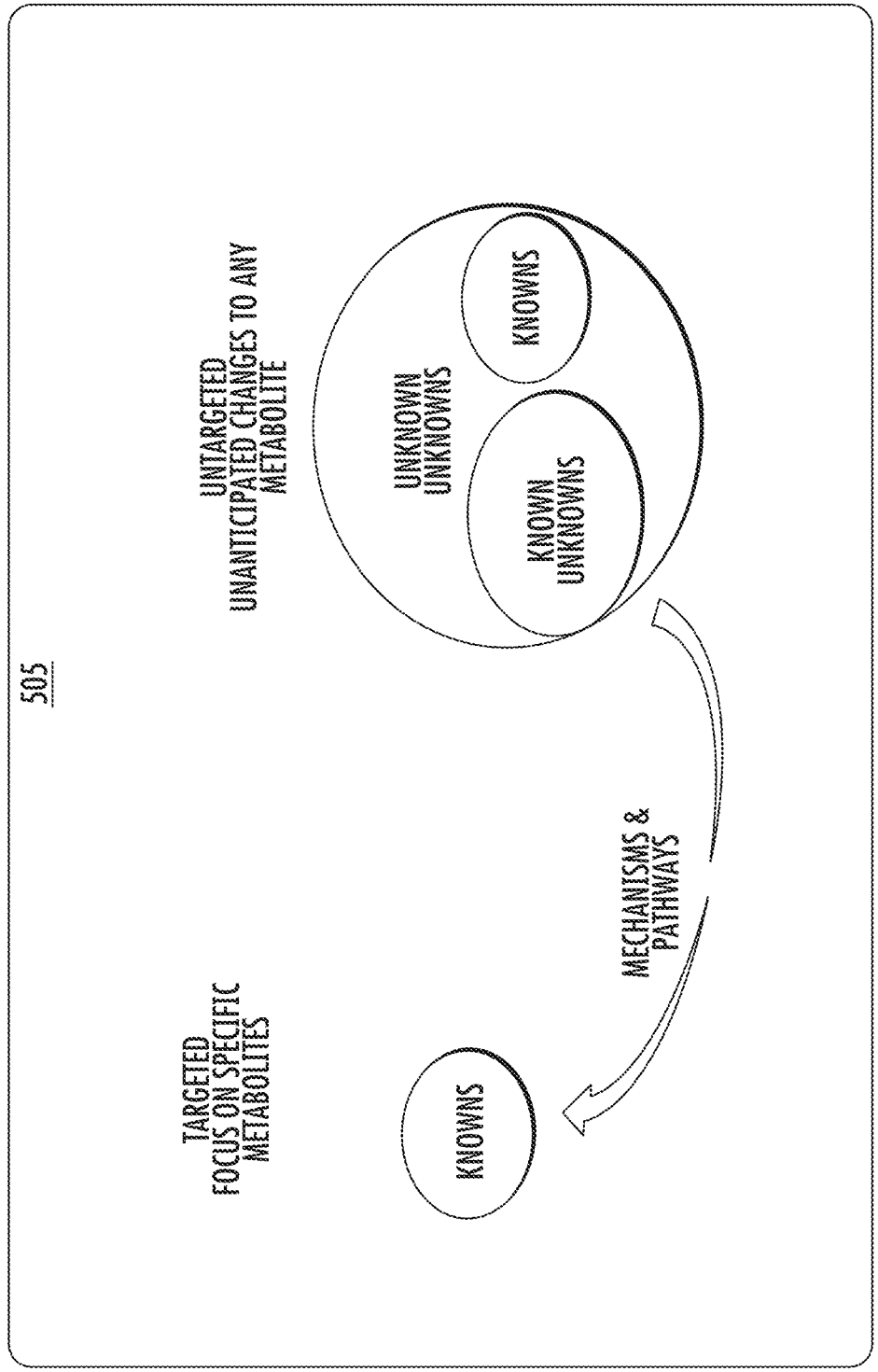
FIG. 5A illustrates targeted and untargeted approaches to a PD profile process according to some embodiments.
Figure 5B:
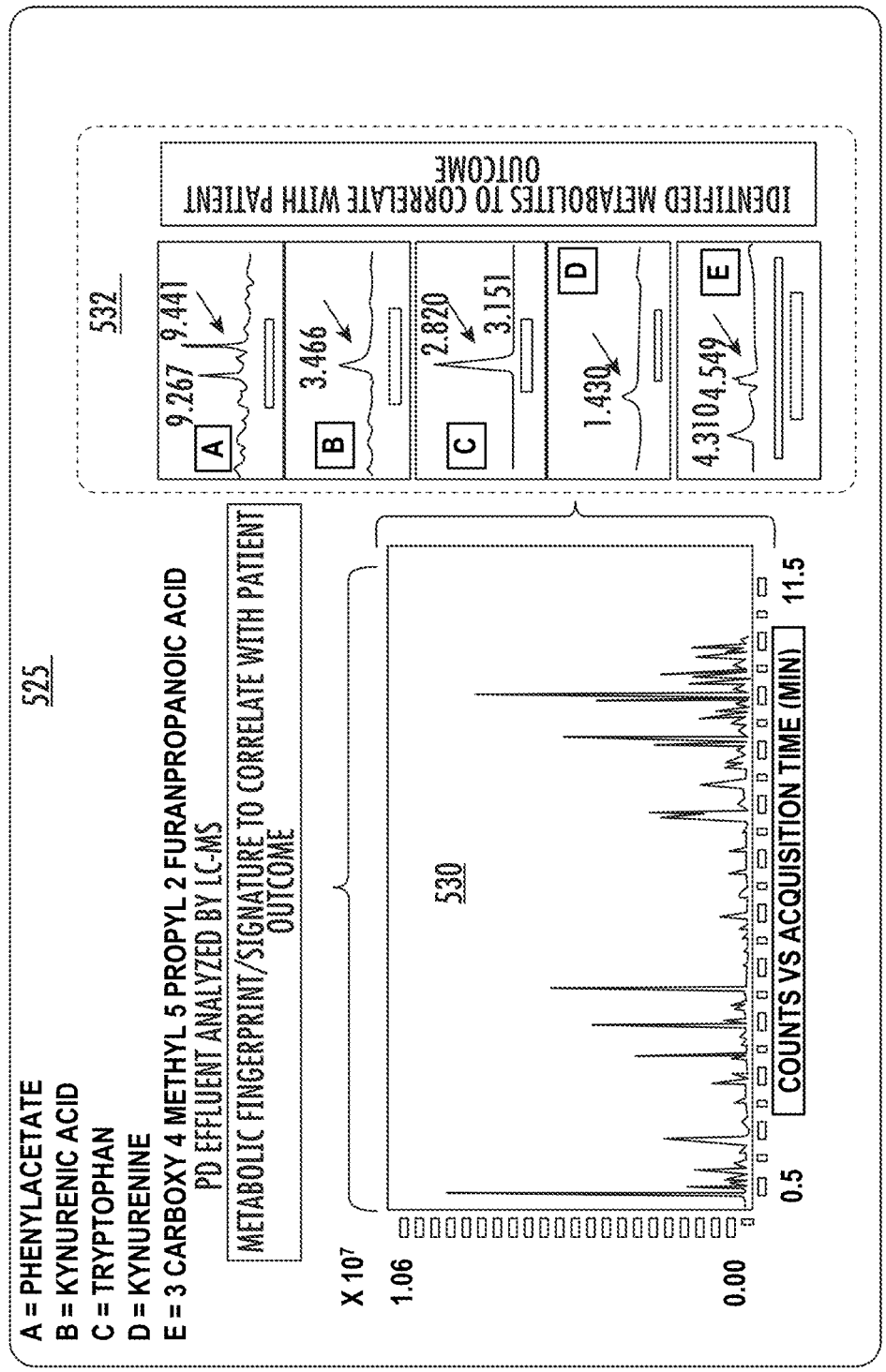
FIG. 5B illustrates exemplary mass analysis results of a PD profile process according to some embodiments.

FIGS. 5A and 5B depict approaches for dialysis profiling processes according to some embodiments. Traditionally, hypothesis-driven approaches have been used to categorize transport status targeting known solutes, such as urea, creatinine, and glucose. In an untargeted approach all molecules, including previously unknowns presented in PD effluent, may be used to generate and/or evaluate patient profile information, such as dialysis adequacy, transport characteristics, and/or the like.

In some embodiments, dialysis profile processes may be combined with machine learning (ML) techniques, including, without limitation, artificial intelligence (AI) processes, neural networks (NN), and/or the like. For example, dialysis profile processes, patient information, profile information, library information, fingerprints, and/or the like may be used in ML/AI applications to analyze, predict, or otherwise patient profiles (e.g., peritoneal transport status and/or classification thereof) and/or to determine a recommended treatment or other course of action based on a patient profile. In various embodiments, library information may be or may include patient profile computational models (e.g., ML processes, AI processes, neural networks (NNs), convoluted neural networks (CNNs), and/or the like. In some embodiments, for example. ML/AI processes may correlate the specific molecular patterns with peritoneal transport status.

For example, in some embodiments, ML/AI algorithms, processes, and/or the like may be used to learn the optimal parameters of the predictive model by investigating past examples with known inputs and known outputs. After training, the predictive model can be used to make predictions on unseen inputs (i.e., generalization). For example, dialysis profile processes may involve a classification supervised learning problem in which the output belongs to a set of distinct classes (e.g., transporter type of a PD patient). Non-limiting types of ML algorithms for building predictive models according to some embodiments may include, without limitation, logistic regression, tree-based methods, Random Forest methods, Gradient Boosting methods, deep learning (DL) algorithms such as Recurrent Neural Networks (RNNs), which process sequence of input, and/or the like. Embodiments are not limited in this context.

Figure 6A:
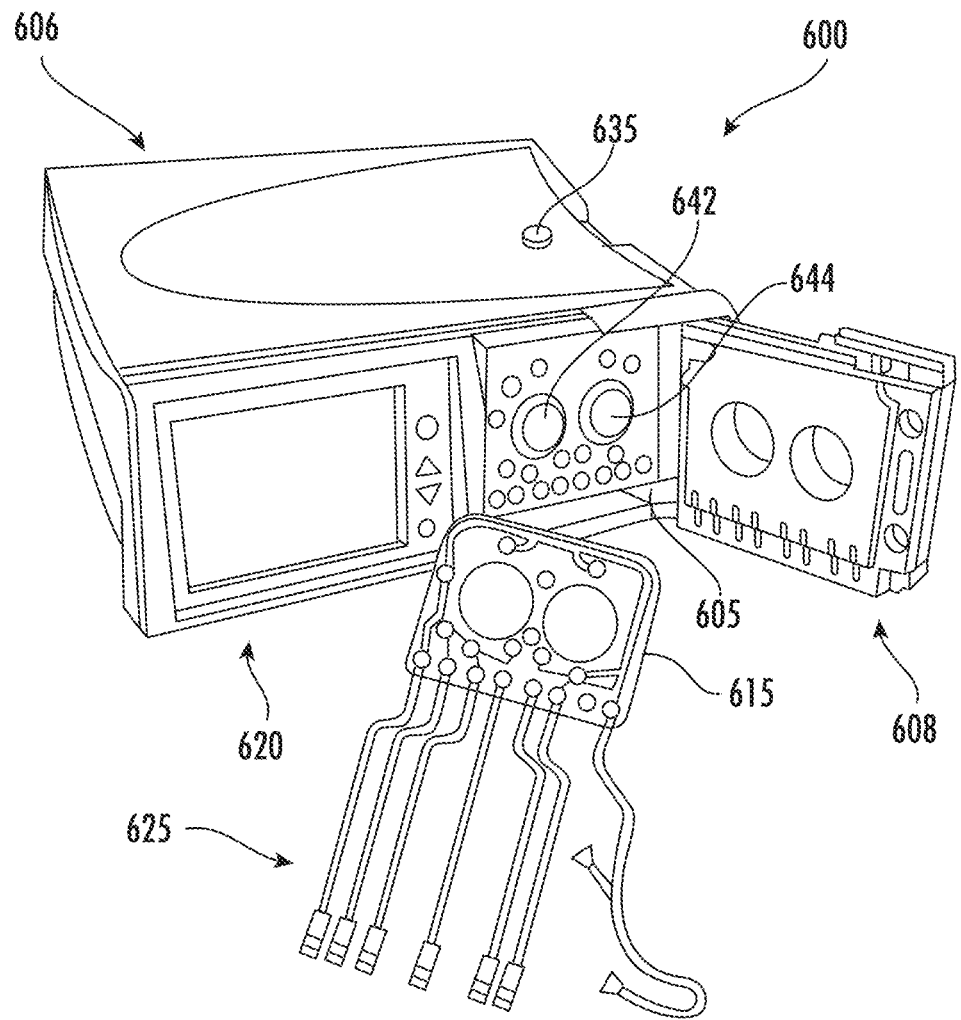
FIGS. 6A and 6B illustrate an exemplary PD system according to some embodiments.
Figure 6B:
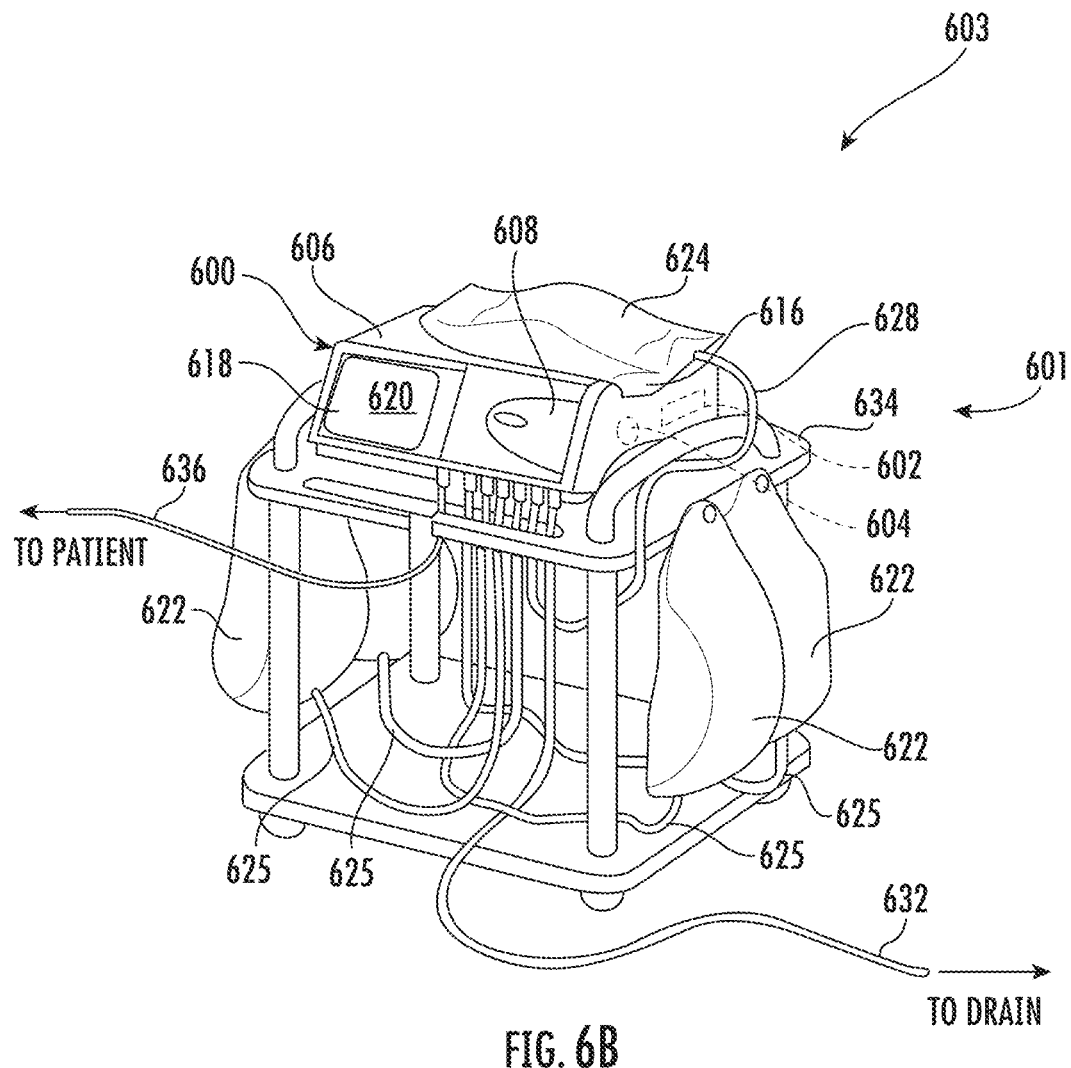

FIGS. 6A-6B show an example of a peritoneal dialysis (PD) system 601, which is configured in accordance with an exemplary embodiment of the system described herein. In some implementations, the PD system 601 may be a home PD system, e.g., a PD system configured for use at a patient's home. The dialysis system 601 may include a dialysis machine 600 (e.g., a peritoneal dialysis machine 600, also referred to as a PD cycler) and in some embodiments the machine may be seated on a cart 634.

The dialysis machine 600 may include a housing 606, a door 608, and a cartridge interface including pump heads 642, 644 for contacting a disposable cassette, or cartridge 615, where the cartridge 615 is located within a compartment formed between the cartridge interface and the closed door 608 (e.g., cavity 605). Fluid lines 625 may be coupled to the cartridge 615 in a known manner, such as via a connector, and may further include valves for controlling fluid flow to and from fluid bags including fresh dialysate and warming fluid. In another embodiment, at least a portion of the fluid lines 625 may be integral to the cartridge 615. Prior to operation, a user may open the door 608 to insert a fresh cartridge 615, and to remove the used cartridge 615 after operation.

The cartridge 615 may be placed in the cavity 605 of the machine 600 for operation. During operation, dialysate fluid may be flowed into a patient's abdomen via the cartridge 615, and spent dialysate, waste, and/or excess fluid may be removed from the patient's abdomen via the cartridge 615. The door 608 may be securely closed to the machine 600. Peritoneal dialysis for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

A heater tray 616 may be positioned on top of the housing 606. The heater tray 616 may be any size and shape to accommodate a bag of dialysate (e.g., a 5 L bag of dialysate) for batch heating. The dialysis machine 600 may also include a user interface such as a touch screen 618 and control panel 620 operable by a user (e.g., a caregiver or a patient) to allow, for example, set up, initiation, and/or termination of a dialysis treatment. In some embodiments, the heater tray 616 may include a heating element 635, for heating the dialysate prior to delivery into the patient.

Dialysate bags 622 may be suspended from hooks on the sides of the cart 634, and a heater bag 624 may be positioned in the heater tray 616. Hanging the dialysate bags 622 may improve air management as air content may be disposed by gravity to a top portion of the dialysate bag 622. Although four dialysate bags 622 are illustrated in FIG. 6B, any number "n" of dialysate bags may be connectable to the dialysis machine 600 (e.g., 1 to 5 bags, or more), and reference made to first and second bags is not limiting to the total number of bags used in a dialysis system 601. For example, the dialysis machine may have dialysate bags 622a, . . . 622n connectable in the system 601. In some embodiments, connectors and tubing ports may connect the dialysate bags 622 and lines for transferring dialysate. Dialysate from the dialysate bags 622 may be transferred to the heater bag 624 in batches. For example, a batch of dialysate may be transferred from the dialysate bags 622 to the heater bag 624, where the dialysate is heated by the heating element 635. When the batch of dialysate has reached a predetermined temperature (e.g., approximately 98°–100° F., 37° C.), the batch of dialysate may be flowed into the patient. The dialysate bags 622 and the heater bag 624 may be connected to the cartridge 615 via dialysate bag lines or tubing 625 and a heater bag line or tubing 628, respectively. The dialysate bag lines 625 may be used to pass dialysate from dialysate bags 622 to the cartridge during use, and the heater bag line 628 may be used to pass dialysate back and forth between the cartridge and the heater bag 624 during use. In addition, a patient line 636 and a drain line 632 may be connected to the cartridge 615. The patient line 636 may be connected to a patient's abdomen via a catheter and may be used to pass dialysate back and forth between the cartridge and the patient's peritoneal cavity by the pump heads 642, 644 during use. The drain line 632 may be connected to a drain or drain receptacle and may be used to pass dialysate from the cartridge to the drain or drain receptacle during use.

Although in some embodiments, dialysate may be batch heated as described above, in other embodiments, dialysis machines may heat dialysate by in-line heating, e.g., continuously flowing dialysate through a warmer pouch positioned between heating elements prior to delivery into a patient. For example, instead of a heater bag for batch heating being positioned on a heater tray, one or more heating elements may be disposed internal to the dialysis machine. A warmer pouch may be insertable into the dialysis machine via an opening. It is also understood that the warmer pouch may be connectable to the dialysis machine via tubing (e.g., tubing 625), or fluid lines, via a cartridge. The tubing may be connectable so that dialysate may flow from the dialysate bags, through the warmer pouch for heating, and to the patient.

In such in-line heating embodiments, a warmer pouch may be configured so dialysate may continually flow through the warmer pouch (instead of transferred in batches for batch heating) to achieve a predetermined temperature before flowing into the patient. For example, in some embodiments the dialysate may continually flow through the warmer pouch at a rate between approximately 100-300 mL/min. Internal heating elements (not shown) may be positioned above and/or below the opening, so that when the warmer pouch is inserted into the opening, the one or more heating elements may affect the temperature of dialysate flowing through the warmer pouch. In some embodiments, the internal warmer pouch may instead be a portion of tubing in the system that is passed by, around, or otherwise configured with respect to, a heating element(s).

The touch screen 618 and the control panel 620 may allow an operator to input various treatment parameters to the dialysis machine 600 and to otherwise control the dialysis machine 600. In addition, the touch screen 618 may serve as a display. The touch screen 618 may function to provide information to the patient and the operator of the dialysis system 601. For example, the touch screen 618 may display information related to a dialysis treatment to be applied to the patient, including information related to a prescription.

The dialysis machine 600 may include a processing module 602 that resides inside the dialysis machine 600, the processing module 602 being configured to communicate with the touch screen 618 and the control panel 620. The processing module 602 may be configured to receive data from the touch screen 618 the control panel 620 and sensors, e.g., weight, air, flow, temperature, and/or pressure sensors, and control the dialysis machine 600 based on the received data. For example, the processing module 602 may adjust the operating parameters of the dialysis machine 600.

The dialysis machine 600 may be configured to connect to a network 603. The connection to network 603 may be via a wired and/or wireless connection. The dialysis machine 600 may include a connection component 604 configured to facilitate the connection to the network 603. The connection component 604 may be a transceiver for wireless connections and/or other signal processor for processing signals transmitted and received over a wired connection. Other medical devices (e.g., other dialysis machines) or components may be configured to connect to the network 603 and communicate with the dialysis machine 600.

The user interface portion such as the touch screen 618 and/or control panel 620 may include one or more buttons for selecting and/or entering user information. The touch screen 618 and/or control panel 620 may be operatively connected to a controller (not shown) and disposed in the machine 600 for receiving and processing the inputs to operate the dialysis machine 600.

Figure 7:
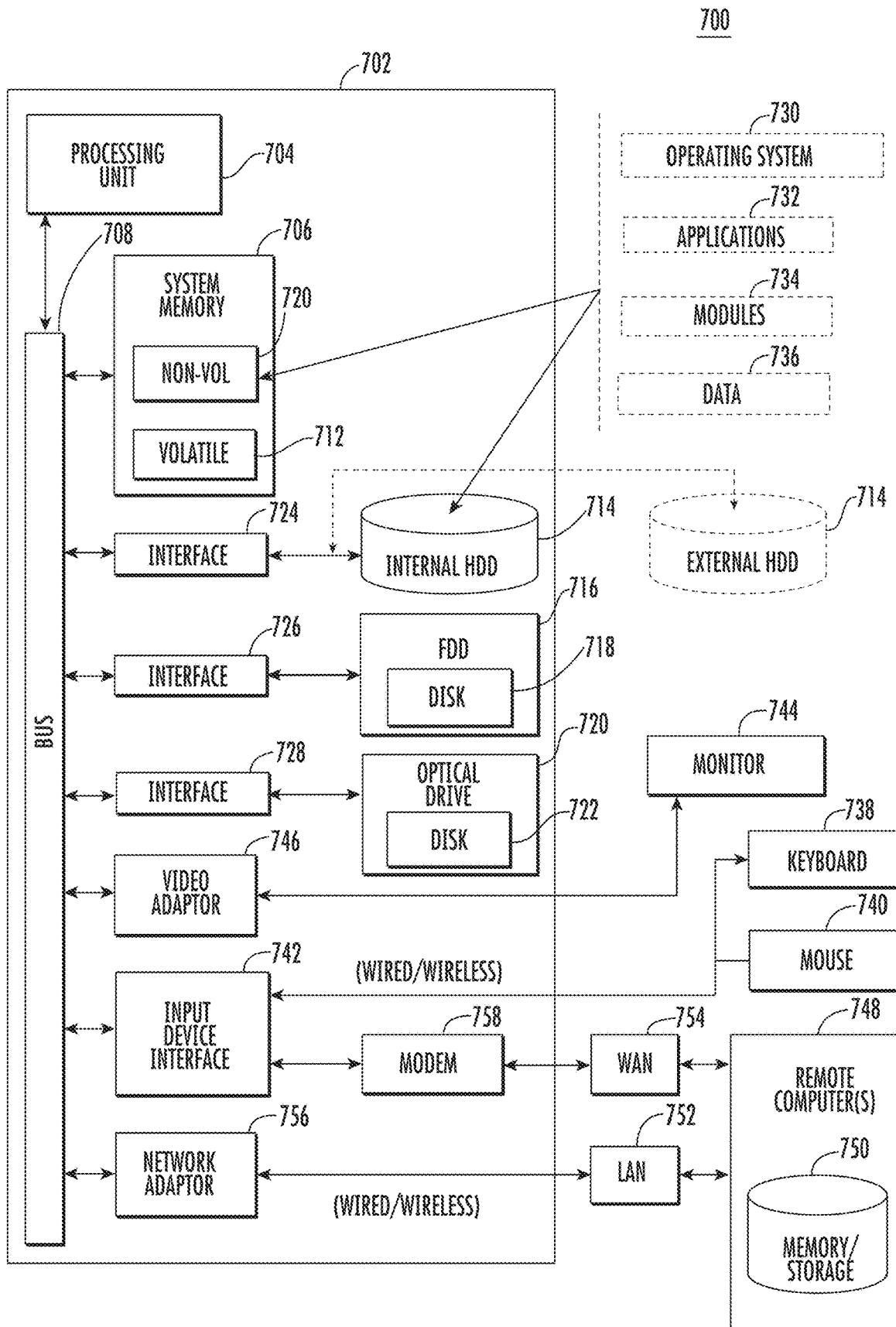
FIG. 7 illustrates an embodiment of a computing architecture in accordance with the present disclosure.

FIG. 7 illustrates an embodiment of an exemplary computing architecture 700 suitable for implementing various embodiments as previously described. In various embodiments, the computing architecture 700 may comprise or be implemented as part of an electronic device. In some embodiments, the computing architecture 700 may be representative, for example, of computing device 702 and/or components thereof. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 700. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 700 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 700.

As shown in FIG. 7, the computing architecture 700 comprises a processing unit 704, a system memory 706 and a system bus 708. The processing unit 704 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 704.

The system bus 708 provides an interface for system components including, but not limited to, the system memory 706 to the processing unit 704. The system bus 708 can be any of several types of bus structure that may further interconnect to a memory bus (with or without a memory controller), a peripheral bus, and a local bus using any of a variety of commercially available bus architectures. Interface adapters may connect to the system bus 708 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 706 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 7, the system memory 706 can include non-volatile memory 710 and/or volatile memory 712. A basic input/output system (BIOS) can be stored in the non-volatile memory 710.

The computer 702 may include various types of computer-readable storage media in the form of one or more lower speed memory units, including an internal (or external) hard disk drive (HDD) 714, a magnetic floppy disk drive (FDD) 716 to read from or write to a removable magnetic disk 718, and an optical disk drive 720 to read from or write to a removable optical disk 722 (e.g., a CD-ROM or DVD). The HDD 714, FDD 716 and optical disk drive 720 can be connected to the system bus 708 by a HDD interface 724, an FDD interface 726 and an optical drive interface 729, respectively. The HDD interface 724 for external drive implementations can include at least one or both of Universal Serial Bus (USB) and IEEE 1384 interface technologies.

The drives and associated computer-readable media provide volatile and/or nonvolatile storage of data, data structures, computer-executable instructions, and so forth. For example, a number of program modules can be stored in the drives and memory units 710, 712, including an operating system 730, one or more application programs 732, other program modules 734, and program data 736. In one embodiment, the one or more application programs 732, other program modules 734, and program data 736 can include, for example, the various applications and/or components of computing device 110.

A user can enter commands and information into the computer 702 through one or more wire/wireless input devices, for example, a keyboard 738 and a pointing device, such as a mouse 740. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 704 through an input device interface 742 that is coupled to the system bus 708, but can be connected by other interfaces such as a parallel port, IEEE 994 serial port, a game port, a USB port, an IR interface, and so forth.

A monitor 744 or other type of display device is also connected to the system bus 708 via an interface, such as a video adaptor 746. The monitor 744 may be internal or external to the computer 702. In addition to the monitor 744, a computer typically includes other peripheral output devices, such as speakers, printers, and so forth.

The computer 702 may operate in a networked environment using logical connections via wire and/or wireless communications to one or more remote computers, such as a remote computer 749. The remote computer 749 can be a workstation, a server computer, a router, a personal computer, portable computer, microprocessor-based entertainment appliance, a peer device or other common network node, and typically includes many or all of the elements described relative to the computer 702, although, for purposes of brevity, only a memory/storage device 750 is illustrated. The logical connections depicted include wire/wireless connectivity to a local area network (LAN) 752 and/or larger networks, for example, a wide area network (WAN) 754. Such LAN and WAN networking environments are commonplace in offices and companies, and facilitate enterprise-wide computer networks, such as intranets, all of which may connect to a global communications network, for example, the Internet.

When used in a LAN networking environment, the computer 702 is connected to the LAN 752 through a wire and/or wireless communication network interface or adaptor 756. The adaptor 756 can facilitate wire and/or wireless communications to the LAN 752, which may also include a wireless access point disposed thereon for communicating with the wireless functionality of the adaptor 756.

When used in a WAN networking environment, the computer 702 can include a modem 758, or is connected to a communications server on the WAN 754, or has other means for establishing communications over the WAN 754, such as by way of the Internet. The modem 759, which can be internal or external and a wire and/or wireless device, connects to the system bus 708 via the input device interface 742. In a networked environment, program modules depicted relative to the computer 702, or portions thereof, can be stored in the remote memory/storage device 750. It will be appreciated that the network connections shown are exemplary and other means of establishing a communications link between the computers can be used.

The computer 702 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

The invention claimed is:

1. A method of determining a peritoneal transport status classification of a dialysis patient, the method comprising:
    performing a dialysis treatment on the dialysis patient based on the peritoneal transport status classification determined via:
        obtaining a volume of peritoneal dialysis (PD) effluent of the dialysis patient;
        generating patient information via mass analysis of the volume of PD effluent of the dialysis patient; and
        determining patient profile information of the dialysis patient based on comparing the patient information with a profile library of mass analysis information of a population of patients with known peritoneal transport status classifications that are used as a baseline to determine the patient profile information, the patient profile information comprising the peritoneal transport status classification for the dialysis patient, the mass analysis information of the population of patients including mass analyses of corresponding volumes of PD effluent for each of the patients in the population, the mass analysis for each of the patients in the population being repeated in a periodic manner over a predetermined time period.

2. The method of claim 1, the mass analysis comprising one of liquid chromatography-mass spectrometry (LC-MS) or mass spectrometry (MS).

3. The method of claim 1, further comprising obtaining the volume during an earlier dialysis treatment of the dialysis patient.

4. The method of claim 1, the volume comprising less than or equal to 1 milliliter (ml).

5. The method of claim 1, the volume comprising 0.005 ml.

6. The method of claim 1, the peritoneal transport status classification comprising classifications of high, high-average, low-average, or low transporters based on solute transport characteristics.

7. The method of claim 1, further comprising determining a dialysis prescription based on the peritoneal transport status classification.

8. The method of claim 1, the profile library comprising a plurality of molecular fingerprints associated with a peritoneal transport status classification.

9. The method of claim 1, the profile library comprising mass analysis information for a plurality of unknown metabolites.

10. An apparatus, comprising:
    at least one memory unit, the at least one memory unit storing:
        instructions;
        patient information generated via mass analysis of a volume of peritoneal dialysis (PD) effluent of a dialysis patient; and
        a profile library of mass analysis information of patients with known peritoneal transport status classifications, the profile library including mass analysis information for a plurality of unknown metabolites; and
    processor circuitry coupled to the at least one memory unit, the processor circuitry to execute the instructions to:
    determine patient profile information based on comparing at least one unknown metabolite in the patient information with at least one of the plurality of unknown metabolites of the profile library, the patient profile information comprising a peritoneal transport status classification.

11. The apparatus of claim 10, the mass analysis comprising one of liquid chromatography-mass spectrometry (LC-MS) or mass spectrometry (MS).

12. The apparatus of claim 10, the volume obtained during routine dialysis of the dialysis patient.

13. The apparatus of claim 10, the volume comprising less than or equal to 1 milliliter (ml).

14. The apparatus of claim 10, the volume comprising 0.005 ml.

15. The apparatus of claim 10, the peritoneal transport status classification comprising classifications of high, high-average, low-average, or low transporters based on solute transport characteristics.

16. The apparatus of claim 10, the profile library comprising a plurality of molecular fingerprints associated with a peritoneal transport status classification.

* * * * *